(12) United States Patent
Koop et al.

(10) Patent No.: US 8,748,652 B2
(45) Date of Patent: Jun. 10, 2014

(54) PROCESS FOR PREPARING IODOPROPARGYL COMPOUNDS

(75) Inventors: Bernd Koop, Köln (DE); Hermann Uhr, Leverkusern (DE); Wolfgang Gausing, Ratingen (DE)

(73) Assignee: LANXESS Deutschland GmbH, Cologne (DE)

( * ) Notice: Subject to any disclaimer, the term of this patent is extended or adjusted under 35 U.S.C. 154(b) by 116 days.

(21) Appl. No.: 13/390,707

(22) PCT Filed: Aug. 26, 2010

(86) PCT No.: PCT/EP2010/062470
§ 371 (c)(1),
(2), (4) Date: Sep. 6, 2012

(87) PCT Pub. No.: WO2011/023757
PCT Pub. Date: Mar. 3, 2011

(65) Prior Publication Data
US 2012/0330051 A1 Dec. 27, 2012

(30) Foreign Application Priority Data
Aug. 31, 2009 (EP) .................................... 09169055

(51) Int. Cl.
*C07C 269/06* (2006.01)
(52) U.S. Cl.
USPC ........................................................ 560/167
(58) Field of Classification Search
CPC .................................................. C07C 269/06
See application file for complete search history.

(56) References Cited

U.S. PATENT DOCUMENTS 5,183,927 A * 2/1993 Utsunomiya et al. ......... 560/115

FOREIGN PATENT DOCUMENTS

| EP | 0014032 A2 | 8/1980 |
| WO | 2005016871 A1 | 2/2005 |

OTHER PUBLICATIONS

Merck, The Merck Index, 10th Edition, 1983, pp. 727, 1236.*
European Search Report for co-pending Application EP09169055 dated Oct. 15, 2009, 2 pages.

* cited by examiner

*Primary Examiner* — Paul A Zucker
(74) *Attorney, Agent, or Firm* — Nicanor A. Kohncke

(57) ABSTRACT

Process for the preparation of iodopropargyl compounds of the formula (I),

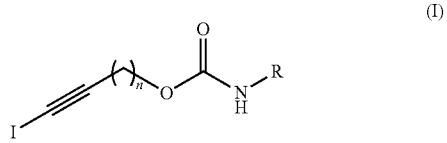

(I)

in which R is hydrogen, in each case optionally substituted $C_1$-$C_{20}$-alkyl, $C_2$-$C_{20}$ alkenyl, $C_6$-$C_{20}$-aryl or $C_3$-$C_{20}$-cycloalkyl
and n is an integer from 1 to 6,
characterized in that propargyl compounds of the formula (II)

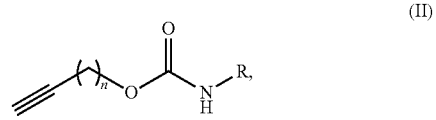

(II)

in which R and n have the above meaning, are reacted with iodine and/or metal iodides in the presence of a base and using chlorine.

8 Claims, No Drawings

PROCESS FOR PREPARING IODOPROPARGYL COMPOUNDS

The present invention relates to a novel process for the preparation of iodopropargyl compounds.

Iodopropargyl compounds are known active ingredients which are used particularly in material protection to protect technical materials such as adhesives, sizes, paper and card, textiles, leather, wood, woodbase materials, paints and plastic articles, cooling lubricants and other materials which can be attacked or destroyed by microorganisms against attack, particularly by fungi. The best known representative is IPBC (3-iodo-2-propynyl-N-butylcarbamate).

It is of particular importance to obtain very clean IPBC during the preparation since polyiodized, for example diiodized or triiodized, compounds, which can arise very readily during the iodization, lead to undesired discoloration, which makes itself known in a negative way during use as microbicide. Furthermore, these impurities often lead to materials protected with IPBC becoming discoloured due to the action of light.

A number of processes for the preparation of iodopropargyl compounds, in particular of IPBC, are already known.

DE-A-2433410 describes, for example, the iodization of propargyl alcohol with iodine, where sodium hypochlorite is used as oxidizing agent for the resulting iodide. This is followed by the reaction of the iodized propargyl alcohol with alkyl isocyanates to give iodopropargyl compounds.

EP-A-14032 describes the reaction of propargyl alcohol with alkyl isocyanates to give propargyl alkylcarbamates and subsequent iodization with iodine or metal iodides using NaOCl as oxidizing agent to give iodopropargyl compounds. As solvent, the use of water with the addition of a cosolvent (e.g. methanol) or of a surfactant or solubility promoter (e.g. partially hydrolyzed polyvinyl acetate) is described.

The iodization of propargyl compounds is described in U.S. Pat. No. 5,693,849 in aqueous medium with iodine and sodium hypochlorite with the addition of an interface-active substance, which is an acidic partial ester of an organic phosphate or the salt of a sulphated fatty alcohol.

WO2005/016871 describes the iodization of propargyl butylcarbamate (PBC) in the aqueous medium with the addition of a nonionic surfactant with metal iodides and sodium hypochlorite as oxidizing agents to give IPBC.

In all of the known processes, sodium hypochlorite is used as oxidizing agent. This is necessary in order to oxidize any iodide which is formed or used and thus to be able to effectively utilize the iodine source. Since the sodium hypochlorite solution used usually has a concentration of only 5-15%, this leads to an undesired dilution of the reaction solution and consequently, following isolation of the product, to a larger amount of wastewater, which has to be disposed of at high cost. Furthermore, sodium hypochlorite has the disadvantage that it readily decomposes, as a result of which the concentration decreases. Consequently, the undesired dilution increases further.

For this reason, sodium hypochlorite solutions have to be stored very carefully. Moreover, during the preparation of sodium hypochlorite, by-products can form, e.g. sodium chlorate, which can likewise lead to undesired secondary reactions when using sodium hypochlorite solutions.

It was therefore an object to find a process in which these disadvantages do not arise.

Surprisingly, a process for the preparation of iodopropargyl compounds of the formula (I) has been found,

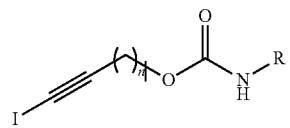

in which R is hydrogen, in each case optionally substituted $C_1$-$C_{20}$-alkyl, $C_2$-$C_{20}$ alkenyl, $C_6$-$C_{20}$-aryl or $C_3$-$C_{20}$-cycloalkyl
and n is an integer from 1 to 6,
characterized in that propargyl compounds of the formula (II)

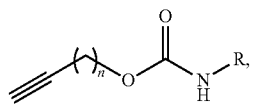

in which R and n have the above meaning, are reacted with iodine and/or metal iodides in the presence of a base and using chlorine.

Preferred optionally substituted $C_2$-$C_{20}$-alkenyls in the meaning of R are vinyl, propenyl or butenyl.

Preferred optionally substituted $C_6$-$C_{20}$-aryls in the meaning of R are phenyl, tolyl or naphthyl.

Preferred optionally substituted $C_3$-$C_{20}$-cycloalkyls in the meaning of R are cyclopropyl, cyclobutyl, cyclopentyl or cyclohexyl.

Suitable preferred substituents for the aforementioned alkenyl, aryl and cycloalkyl radicals are methyl, ethyl, n-propyl, isopropyl, chlorine, bromine, fluorine, methoxy, ethoxy, dimethylamino, methoxycarbonyl, ethoxycarbonyl, hydroxy and acyl.

Suitable preferred substituents for the aforementioned alkyl radical are chlorine, bromine, fluorine, methoxy, ethoxy, dimethylamino, methoxycarbonyl, ethoxycarbonyl, hydroxy, acyl and phenyl.

Preference is given to compounds of the formula (I) in which R in the meaning of the $C_1$-$C_{20}$-alkyl radical is optionally substituted $C_7$-$C_{20}$-alkylaryl, in particular benzyl or phenylethyl or $C_1$-$C_6$-alkyl, such as methyl, ethyl, n-propyl, isopropyl or n-butyl and n is Particularly preferably, R is n-butyl and n is 1.

It is preferred to carry out the process according to the invention in water and/or an organic solvent. In the case of mixtures, the ratio of water to organic solvent is preferably 9:1 to 1:9, in particular 3:1 to 1:3.

Of suitability are various organic solvents, such as e.g. aliphatic hydrocarbons, aromatic hydrocarbons, alcohols, ethers, chlorinated hydrocarbons, nitriles, esters or ketones. Mixtures of two or more solvents can also be used.

Furthermore, water by itself can be used, optionally in combination with one or more organic solvents, in particular aliphatic alcohols, preferably methanol and/or ethanol.

When using water, optionally together with an organic solvent, surface-active substances can be co-used, e.g. nonionic, anionic, amphoteric or cationic emulsifiers, such as e.g. betaines, polyoxyethylene fatty acid esters, polyoxyethylene fatty alcohol ethers, alkylaryl polyglycol ethers, alkylsulphonates, alkyl sulphates, arylsulphonates, and also alcohol ethoxylates, in particular ethoxylates of $C_{10}$-$C_{18}$-alcohols. Furthermore, phase transfer catalysts can be used, such as e.g. tetrabutylammonium hydrogensulphate, tetrabutylammonium bromide, tetrabutylammonium chloride, tetraoctylammonium bromide, tetraoctylammonium chloride, methyltridecylammonium chloride, methyltrioctyl-ammonium chloride (Aliquat 336) or methyltributylammonium chloride.

A suitable iodine source is elemental iodine ($I_2$) and/or metal iodides, such as, for example, sodium iodide, potassium iodide, or mixtures. These compounds can be used as solid or dissolved in a suitable solvent, in particular alcohols such as methanol or ethanol and/or water.

In the case of iodine ($I_2$), this is preferably used in an amount of from 0.4 to 0.75 mol equivalents, in particular 0.45 to 0.6 mol equivalents, based on the propargyl compound of the formula (II) used. In the case of metal iodide, this is preferably used in an amount of from 0.8 to 1.5 mol equivalents, in particular 0.9 to 1.2 mol equivalents, based on the propargyl compound of the formula (II) used.

Here, the total amount of iodine or metal iodide can already be present at the start of the reaction, or only some is present, with the remainder being added continuously or discontinuously, e.g. in portions, in the course of the reaction.

The process according to the invention is carried out in the presence of a base. Suitable bases are, for example, alkali metal hydroxides, phosphates, alcoholates and carbonates, and mixtures thereof. Of particular suitability from the series of the alkali metal hydroxides are NaOH and KOH, and from the series of the carbonates $Na_2CO_3$, $K_2CO_3$, $MgCO_3$. Very particular preference is given to using aqueous solutions of NaOH and/or KOH. The base is preferably used, based on the propargyl compound of the formula (II), in a molar ratio of from 1:1 to 10:1, preferably from 1:1 to 5:1.

The chlorine used is preferably used in an amount of from 0.7 to 5 mol equivalents, preferably 1 to 2 mol equivalents, based on the iodine ($I_2$) or metal iodide used.

The chlorine is preferably introduced into the reaction medium as gas during the reaction. The rate is preferably selected such that the process according to the invention is preferably carried out at $-20$ to $+30°$ C., in particular at $-10$ to $+10°$ C., particularly preferably at 0 to $10°$ C.

To carry out the process according to the invention, the procedure generally involves initially introducing the propargyl compound of the formula (II) in a solvent, preferably adjusting the reaction temperature, then adding the base and optionally further additives, and then metering in the iodine source in its entirety or gradually at a suitable rate, either as solid or dissolved in a suitable solvent. The chlorine is then introduced into the reaction medium preferably at a suitable rate such that the reaction temperature preferably does not exceed the desired temperature. When the reaction is complete, depending on the reaction medium used for the work-up, the compound of the formula (I) can be isolated e.g. by means of extraction with a solvent that is immiscible with the reaction medium, or directly from the reaction medium by filtration. When using water with co-use of an organic solvent, it is also possible to remove some or all of the organic solvent by distillation and to then isolate the precipitated compound of the formula (I) by filtration.

If required, the resulting compound of the formula (I) can also be recrystallized. For this purpose, preference is given to using mixtures of aliphatic alcohols, such as methanol or ethanol and water.

The process according to the invention leads to considerably lower contents in the wastewater compared with oxidizing agents such as hypochlorite which can only be used in diluted form. It is also surprising that the reactive chlorine does not react with the triple bond and forms no undesired by-products. No chlorine addition compounds onto the triple bond were found.

The following examples serve to illustrate the process according to the invention without, however, limiting it.

EXAMPLES

Example 1

At $5°$ C., 4.5 g of $C_{12}$-$C_{16}$-alcohol ethoxylate, 16.9 g of propargyl butylcarbamate (0.107 mol), 40.7 g of NaI solution (40% strength, 0.108 mol) and 25.8 g of NaOH solution (50% strength, 0.322 mol) are introduced as initial charge in 330 g of water. Chlorine (10.3 g, 0.145 mol) is then slowly introduced into the reaction mixture such that the temperature remains below $5°$ C. When the introduction is complete, the mixture is slowly heated to $20°$ C. and stirred at this temperature for 4 h. The precipitated solid is then isolated by filtration, washed with water and dried in vacuo. This gives 26.1 g of 3-iodo-2-propynyl N-10 butylcarbamate (purity: 95.4% (HPLC), polyiodized compounds: <0.1% (HPLC), yield: 83%).

Example 2

At $8°$ C., 10.1 g of sodium hydroxide (0.244 mol) and 19.0 g of propargyl butylcarbamate (0.122 mol) are introduced as initial charge in 48 g of methanol and 50 g of water. At this temperature, 15.5 g of iodine (0.061 mol) are added in portions. Chlorine (5.6 g, 0.079 mol) is then slowly introduced into the reaction mixture so that the temperature still remains below $8°$ C. When the metered addition is complete, the mixture is stirred for 1 h at this temperature and then 105 g of water are added. The precipitated solid is isolated by filtration, washed with water and dried in vacuo. This gives 28.5 g of 3-iodo-2-propynyl N-butylcarbamate (purity: 95.0% (HPLC), polyiodized compounds: 0.3% (HPLC), yield: 79%).

Example 3

At $5°$ C., 19.0 g of propargyl butylcarbamate (0.122 mol), 12.2 g of sodium hydroxide (0.305 mol) and 18.5 g of sodium iodide (0.123 mol) are introduced as initial charge in 50 g of water and 48 g of methanol. Chlorine (11.7 g, 0.165 mmol) is then slowly introduced so that the temperature remains below $5°$ C. When the metered addition is complete, the mixture is stirred at this temperature for 1 h, then slowly heated to room temperature and stirred for 1 hour. After adding 100 g of water, the precipitated solid is isolated by filtration, washed with water and dried in vacuo. This gives 29.1 g of 3-iodo-2-propynyl N-butylcarbamate (purity: 94.7% (HPLC), polyiodized compounds: <0.1% (HPLC), yield: 80%).

What is claimed is:

1. A process for the preparation of iodopropargyl compounds of the formula (I),

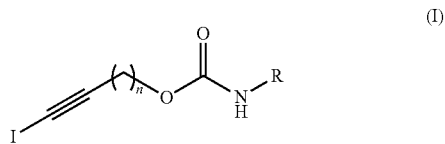

in which R is hydrogen, in each case optionally substituted $C_1$-$C_{20}$-alkyl, $C_2$-$C_{20}$-alkenyl, $C_6$-$C_{20}$-aryl or $C_3$-$C_{20}$-cycloalkyl
and n is an integer from 1 to 6, comprising:
reacting a propargyl compounds of the formula (II)

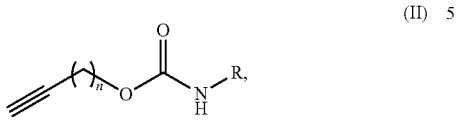

(II)

in which R and n have the above meaning, with an iodine source, wherein said iodine source is elemental iodine and/or a metal iodide,
and wherein said reacting step is performed in the presence of a base with the addition of gaseous chlorine.

2. The process according to claim 1, wherein R is $C_1$-$C_6$-alkyl and n is 1.

3. The process according to claim 1, wherein R is n-butyl and n is 1.

4. The process according to claim 1, wherein the iodine source is the elemental iodine.

5. The process according to claim 1, wherein the iodine source is the metal iodide.

6. The process according to claim 1, wherein the reacting step is performed in water and/or an organic solvent.

7. The process according to claim 1, wherein the reacting step is performed in an aqueous medium comprising at least one organic solvent.

8. The process according to claim 5, wherein the metal iodide is Sodium Iodide and/or Potassium Iodide.

* * * * *